United States Patent
Langeveld et al.

(10) Patent No.: US 8,054,937 B2
(45) Date of Patent: Nov. 8, 2011

(54) SYSTEMS AND METHODS FOR USING AN INTENSITY-MODULATED X-RAY SOURCE

(75) Inventors: Willem G. J. Langeveld, Menlo Park, CA (US); William A. Johnson, La Honda, CA (US); Roger D. Owen, Modesto, CA (US); Russell G. Schonberg, Los Altos Hills, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 119 days.

(21) Appl. No.: 12/484,172

(22) Filed: Jun. 12, 2009

(65) Prior Publication Data

US 2010/0034355 A1 Feb. 11, 2010

Related U.S. Application Data

(60) Provisional application No. 61/087,810, filed on Aug. 11, 2008.

(51) Int. Cl.
*G01N 23/04* (2006.01)
(52) U.S. Cl. .......................................... 378/57; 378/106
(58) Field of Classification Search .................... 378/51, 378/53, 54, 55, 57, 65, 108, 62, 101, 106
See application file for complete search history.

(56) References Cited

U.S. PATENT DOCUMENTS

| 5,321,271 A | 6/1994 | Schnonberg et al. ...... 250/492.3 |
| 5,418,372 A | 5/1995 | Schnonberg et al. ...... 250/492.3 |
| 5,661,377 A | 8/1997 | Mishin et al. ................. 315/505 |
| 5,949,811 A * | 9/1999 | Baba et al. ..................... 378/108 |
| 6,459,761 B1 | 10/2002 | Grodzins et al. ................ 378/57 |
| 7,272,208 B2 | 9/2007 | Yatsenko et al. .............. 378/145 |
| 2005/0117683 A1 | 6/2005 | Mishin et al. ................. 376/157 |
| 2008/0211431 A1 | 9/2008 | Mishin et al. ................. 315/505 |

FOREIGN PATENT DOCUMENTS

| WO | WO-A 0159485 | 8/2001 |
| WO | WO 2009027667 | 3/2009 |

* cited by examiner

*Primary Examiner* — Courtney Thomas
(74) *Attorney, Agent, or Firm* — Novel IP

(57) ABSTRACT

The present invention is directed toward an X-ray scanning system having a plurality of detectors and a controller, where a) the controller is configured to receive and identify a minimum X-ray transmission level detected by at least one detector, b) the controller compares the minimum X-ray transmission level to at least one predetermined threshold transmission level, and c) based on said comparison, the controller generates an adjustment signal. The present invention further comprises an X-ray source, where the X-ray source receives an adjustment signal and is configured to adjust an X-ray pulse duration based on the adjustment signal.

20 Claims, 7 Drawing Sheets

US 8,054,937 B2

SYSTEMS AND METHODS FOR USING AN INTENSITY-MODULATED X-RAY SOURCE

CROSS-REFERENCE TO RELATED APPLICATIONS

The present invention relies on U.S. Provisional Patent Application No. 61/087,810, which was filed on Aug. 11, 2008.

FIELD OF THE INVENTION

The present invention generally relates to the field of radiant energy imaging systems, and more specifically to systems and techniques for detecting special nuclear materials (SNM) and other contraband using high intensity X-ray radiation sources. In particular, the present invention relates to improved methods and systems for delivering the minimum X-ray intensity needed to sufficiently penetrate cargo, and therefore detect SNM and other contraband.

BACKGROUND OF THE INVENTION

X-ray radiography imaging of cargo containers and trucks for the detection of Special Nuclear Material (SNM) and other contraband requires high-intensity X-ray radiation sources. The higher the intensity at a specific source energy, the greater the amount of material the X-ray beam can penetrate, and the better the resulting contrast and resolution. In conventional practice, the X-ray source intensity of an inspection system is set to the highest level allowable under the particular circumstances of the system and the inspection area, referred to as the Output Set Point (OSP) of the source, and all cargo is inspected using this fixed intensity, whether an accurate inspection of the cargo requires this intensity or not. This OSP is typically not the highest rated intensity that the source is capable of producing. More often than not, the OSP is set so that the source does not exceed a predetermined specified radiation dose limit at the boundary of a predefined exclusion zone, or, in the case of a portal inspection system (where truck drivers drive their trucks through the inspection system), to stay below a certain dose limit to the driver of the inspected truck.

While conventional inspection systems are capable of providing higher cargo penetration, they are inefficient in that they do not take advantage of the rated maximum intensity of the source, which is usually higher than the OSP. In addition, conventional inspection systems use much higher intensity than needed for certain cargos (or portions thereof), leading, on average, to unnecessarily high radiation levels around the inspection system.

What is needed therefore is an inspection system and method of using such inspection system that has the capability of delivering the minimum X-ray intensity needed to sufficiently image and/or penetrate cargo.

What is also needed is a mobile or truck mounted inspection system and method that is capable of using an intensity-modulated 6 MeV or higher X-ray source with consideration for weight-bearing and shielding requirements.

SUMMARY OF THE INVENTION

The present invention is directed toward an X-ray scanning system comprising a plurality of detectors, a controller, wherein said controller is configured to receive and identify a minimum X-ray transmission level detected by at least one of said plurality of detectors, wherein said controller compares said minimum X-ray transmission level to at least one predetermined threshold transmission level, and wherein, based on said comparison, said controller generates an adjustment signal, and an X-ray source, wherein said X-ray source receives said adjustment signal and is configured to adjust an X-ray pulse duration based on said adjustment signal.

Optionally, the X-ray source is a linear accelerator having an energy in a range of 1 MeV to 15 MeV. The X-ray source comprises a controller that receives said adjustment signal and, based on said signal, adjusts an X-ray pulse duration. The controller compares said minimum X-ray transmission level to a first predetermined threshold and, if said minimum X-ray transmission level is below said first predetermined threshold, generates an adjustment signal that causes said X-ray source to increase an X-ray pulse duration. Alternatively, the controller compares said minimum X-ray transmission level to a first predetermined threshold and second predetermined threshold and, if said minimum X-ray transmission level is above said first predetermined threshold but below said second predetermined threshold, generates an adjustment signal that causes said X-ray source to not modify an X-ray pulse duration. Alternatively, the controller compares said minimum X-ray transmission level to a first predetermined threshold and second predetermined threshold and, if said minimum X-ray transmission level is above said second predetermined threshold, generates an adjustment signal that causes said X-ray source to decrease an X-ray pulse duration.

Optionally, the controller comprises a computer having a processing unit and wherein said processing unit interfaces with an input/output board that receives signals from at least one of said plurality of detectors. The processing unit is at least one of a field programmable gate array or an application specific integrated circuit.

Optionally, the plurality of detectors comprise a first detector array, said first detector array being configured to measure a required source intensity for a subsequent X-ray pulse, and a second detector array, said second detector array being configured to measure a transmission image and not said required source intensity. The X-ray source is configured to adjust a duration of a second X-ray pulse based on an adjustment signal generated from a first X-ray pulse occurring immediately prior to said second X-ray pulse.

In another embodiment, the present invention is directed toward a method of retrofitting an existing X-ray scanning system having an X-ray source, a penetration capability, a radiation footprint, and a plurality of detectors, comprising installing a controller, wherein said controller is configured to receive and identify a minimum X-ray transmission level detected by at least one of said plurality of detectors, wherein said controller compares said minimum X-ray transmission level to at least one predetermined threshold transmission level, and wherein, based on said comparison, said controller generates an adjustment signal, said adjustment signal being configured to adjust an X-ray pulse duration based on said adjustment signal.

Optionally, the X-ray source is a linear accelerator having an energy in a range of 1 MeV to 15 MeV. The penetration capability is increased by a distance ranging from 1 cm to 10 cm. The average radiation footprint is improved by a factor between 1 and 9. The controller compares said minimum X-ray transmission level to a first predetermined threshold and, if said minimum X-ray transmission level is below said first predetermined threshold, generates an adjustment signal that causes said X-ray source to increase an X-ray pulse duration. Alternatively, the controller compares said minimum X-ray transmission level to a first predetermined threshold and second predetermined threshold and, if said minimum X-ray transmission level is above said first predetermined threshold but below said second predetermined threshold, generates an adjustment signal that causes said X-ray source to not modify an X-ray pulse duration. Alternatively, the controller compares said minimum X-ray transmission level to a first predetermined threshold and second predetermined threshold and, if said minimum X-ray transmission level is above said second predetermined threshold, generates an adjustment signal that causes said X-ray source to decrease an X-ray pulse duration.

Optionally, the controller comprises a computer having a processing unit and wherein said processing unit interfaces with an input/output board that receives signals from at least one of said plurality of detectors. The plurality of detectors comprise a first detector array, said first detector array being configured to measure a required source intensity for a subsequent X-ray pulse, and a second detector array, said second detector array being configured to measure a transmission image and not said required source intensity. The X-ray source is configured to adjust a duration of a second X-ray pulse based on an adjustment signal generated from a first X-ray pulse occurring immediately prior to said second X-ray pulse.

BRIEF DESCRIPTION OF THE DRAWINGS

These and other features and advantages of the present invention will be appreciated, as they become better understood by reference to the following Detailed Description when considered in connection with the accompanying drawings, wherein.

DETAILED DESCRIPTION OF THE INVENTION

Figure 1A:
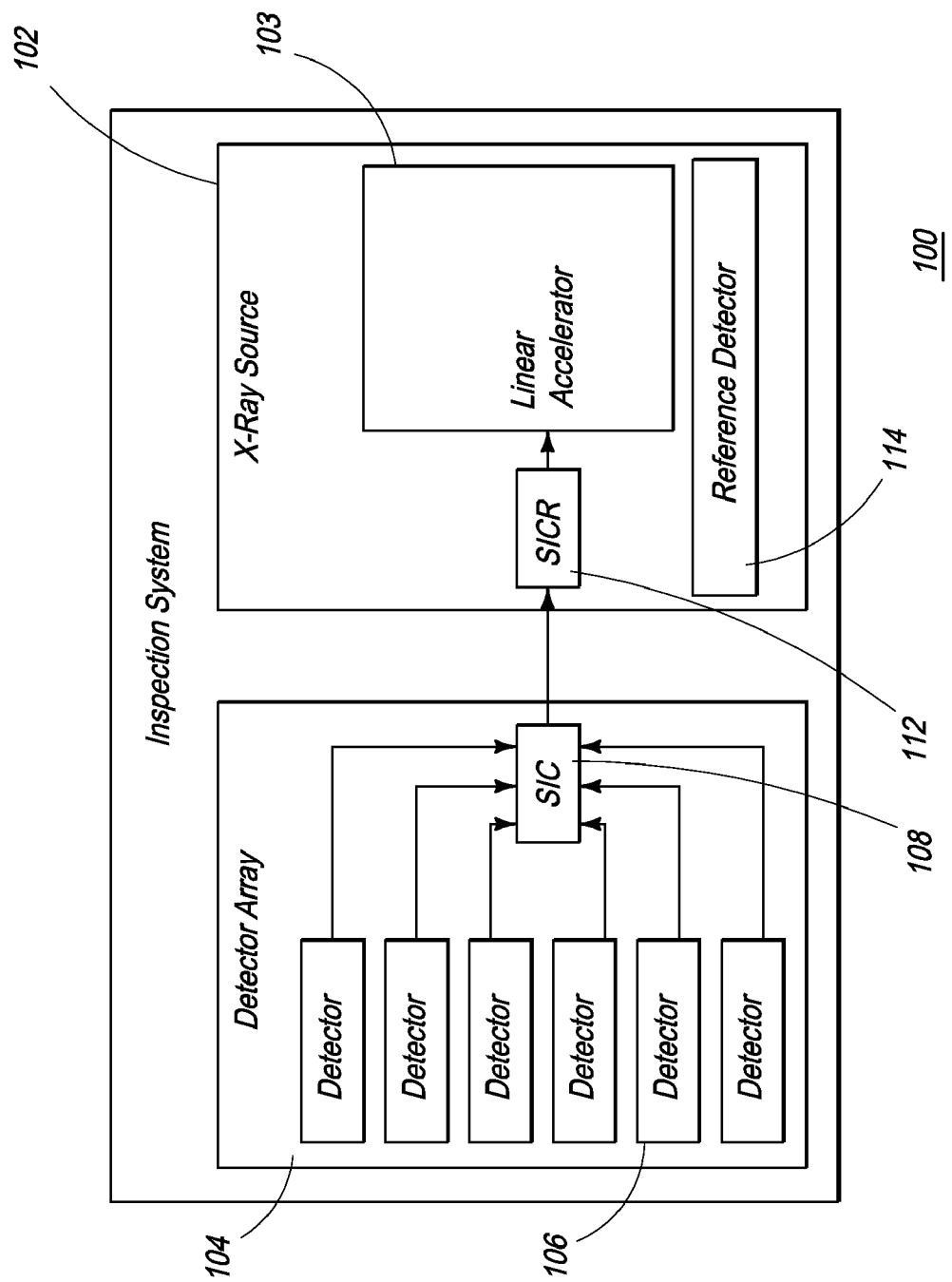
FIG. 1a shows a diagram of one embodiment of a cargo inspection system.

X-ray cargo inspection systems for the detection and verification of threats and contraband must address competing performance requirements. High X-ray intensity is needed to penetrate dense cargo, while low intensity is desirable to minimize the radiation footprint (the size of the controlled area), required shielding and the dose to personnel.

Most X-ray sources used for the purposes of cargo inspection are linear-accelerator based, where electrons are discharged from an electron gun in a pulsed fashion. These electrons are then accelerated in a linear accelerator up to a certain kinetic energy. For typical sources used in the industry, this kinetic energy is between 1 and 15 MeV, including 1 MeV, 4 MeV, 4.5 MeV, 6 MeV, and 9 MeV. The accelerated electrons then strike a target made of a dense material, such as (but not limited to) tungsten, causing the release of X-rays, which are then used in the inspection system. The average intensity of the X-ray beam is directly proportional to the number of electrons striking the target per second. Electrons are charged, and the total charge striking the target, per second, is called the average electron current (in MeV) in the accelerator.

Linear accelerators are pulsed devices, with each pulse lasting, typically, a few microseconds. Average current is determined by using peak current in the accelerator, the number of pulses per second, and the duration of each pulse. The peak current in the accelerator is the current of electrons, as measured during an actual pulse. Because each pulse lasts only a short time, and there are not very many pulses each second (up to about ~400), the average current in the accelerator is much smaller than the peak current—most of the time there is no electron current in the accelerator at all.

There are, therefore, three ways to control the average electron current in the accelerator and, hence, the average X-ray output intensity of the source: the peak current, the number of pulses per second, and the pulse duration. When conventional sources are used, they are preset to a fixed intensity by, for example, adjusting the peak current of the accelerator, and a number of other properties, not only of the X-ray source itself, but also of the modulator (which provides proper phasing and timing of the radio-frequency (RF) electromagnetic waves used to accelerate the electrons) and the RF source itself. Typically, this is done in such a fashion as not to change the pulse duration or the electron kinetic energy. A change of the intensity of the source after the fact can be accomplished but usually requires a service call from the manufacturer.

Existing sources operate at a fixed X-ray intensity, which is referred to as the Output Set Point (OSP). For much of a typical image, the OSP is higher than needed, and performance may be limited when the OSP is chosen to be less than the maximum rated output of the source to reduce the radiation footprint.

Thus, an intensity-modulated X-ray source can be used to significantly enhance the imaging penetration performance of cargo inspection systems while maintaining the same average radiation footprint in terms of size of exclusion zone and radiation dose to cargo and personnel.

The present invention is directed towards improved methods and systems for delivering, on a pulse-to-pulse basis, just the X-ray intensity needed for sufficient imaging penetration of the cargo to detect SNM and other contraband. The present invention preferably modulates the pulse duration, thereby eliminating fluctuations in energy that would arise from modifying the peak current and avoiding the complexities associated with modifying pulse rates.

The present invention is also directed towards improved methods and systems for varying, on a pulse-to-pulse basis, the X-ray intensity of the source, based on the signal strengths measured in the inspection system's detector array during the previous pulse.

The present invention is also directed towards a feed-back system in which the intensity of a standard linear-accelerator-based pulsed X-ray source can be changed in a plurality of ways, including by changing the pulse width and/or the peak beam current, under computer control from one pulse to the next. Thus, the system uses the measured X-ray intensities as part of a feedback loop to modulate the intensity of the X-ray source.

The present invention is also directed towards a cargo inspection system employing a linear-accelerator-based x-ray source, where, with a 6 MeV source, it is capable of achieving up to two inches greater penetration capability of steel (or steel-equivalent) than conventional systems, while on average producing the same or smaller radiation footprint as present fixed-intensity sources. In particular, the present invention can be used to retrofit an existing X-ray system to improve the average radiation footprint by a factor of between 1 and 3 and improve penetration by a distance of 1 to 5 cm steel or steel-equivalent.

With X-ray sources of energies other than 6 MeV, the above performance figures may be different; however, the performance is expected to improve with increasing X-ray source energy. For example, in a system having electrons with an accelerated kinetic energy ranging from 1 MeV to 15 MeV, with 1 MeV typically representing a smaller degree of penetration, the system and method of the present invention has the potential to improve the radiation footprint (reduce it) from a low factor of 1.05 to 2 for a 1 MeV energy source to a high factor of 5 to 10 for a 15 MeV energy source and has the potential to increase the penetration a distance of 0.5 to 1 cm for 1 MeV to a distance of about 5 to 10 cm for 15 MeV.

Thus, the present invention is directed towards a cargo inspection system that is capable of anticipating the x-ray intensity needed for each pulse by evaluating signal strength in the cargo inspection system detector array for the previous pulse.

The present invention is thus directed towards a linear accelerator (linac)-based X-ray source that is capable of 1) changing intensity from one pulse to the next via an electronic signal and 2) determining the required source intensity for the next pulse via detector array electronics.

In addition, the present invention is directed towards a cargo inspection system that employs a relatively small linear accelerator system with its respective shielding, as compared to comparable conventional sources.

The present invention is also directed towards a mobile or truck mounted inspection system and method that is capable of using an intensity-modulated 6 MeV or higher X-ray source with consideration for weight-bearing and shielding requirements.

The present invention is directed towards multiple embodiments. Reference will now be made to specific embodiments of the present invention. The embodiments described herein are not a general disavowal of any one specific embodiment or used to limit the claims beyond the meaning of the terms used therein. It should be noted that while the present invention can be used with any inspection system, having any type of radiation source and detector array, the present invention is described with respect to a cargo inspection system that typically employs linear accelerator-based pulsed high-energy X-ray sources. Thus, the description is by no means to be construed as limiting.

Referring to FIG. 1a, in one embodiment, the cargo inspection system 100 of the present invention comprises an X-ray source 102 and a detector array 104. The detector array 104 comprises a plurality of detectors 106 and a Source Intensity Controller (SIC) 108, which further comprises suitable electronics and interconnects to determine, for a given X-ray pulse, the X-ray transmission in the plurality of detectors 106 in the detector array 104 and to find the detector which has recorded the minimum transmission level. The SIC 108 then determines whether the minimum transmission level is below a predetermined and preprogrammed first level A; or above a predetermined and preprogrammed first level A, but below a predetermined and preprogrammed second level, B; or above a predetermined and preprogrammed second level B. In one embodiment, A has a value of 300 and B has a value of 600, in arbitrary units.

It should be noted herein that the SIC can be implemented in a plurality of embodiments, as is obvious to those of ordinary skill in the art. In one embodiment, the present invention employs a commercially available embedded computer with an FPGA. The FPGA interfaces to a custom I/O board which reads the signals from the detector array. The FPGA has custom firmware which performs the calculations described above, determines the required signal that needs to be sent to the X-ray source, and subsequently sends that signal to the X-ray source. It should also be noted herein, as evident to those of ordinary skill in the art, that it is possible to use an ASIC versus an FPGA.

In each case, the SIC 108 sends a signal, either along an electrical and/or an optical connection, or wirelessly, to the X-ray source 102. If the minimum transmission level is below a predetermined and preprogrammed first level A, a first signal instructs the X-ray source 102 to increase its X-ray intensity for the next pulse. Optionally, if the minimum transmission level is above a predetermined and preprogrammed first level, A, but below a predetermined and preprogrammed second level B, a second signal instructs the source to stay at the same intensity. It should be noted, however, that the second signal may be eliminated and the source will stay at the same intensity by default. If the minimum transmission level is above a predetermined and preprogrammed second level B, a third signal instructs the source to decrease its X-ray intensity for the next pulse. A fourth signal is used to instruct the source to perform the X-ray pulse itself. This last signal is sent after a predetermined period of time has elapsed for the source to settle in its new intensity setting.

The present invention is capable of modulating the intensity of the X-ray source 102 on a pulse-to-pulse basis (i.e. in a few milliseconds). In one embodiment, the X-ray source 102 is modified so that the system 100 is capable of pulse-to-pulse variation of intensity. In one embodiment, the X-ray source 102 further comprises a linear accelerator 103. In one embodiment, the X-ray source 102 further comprises a Source Intensity Control Receiver (SICR) 112, which is an electronics circuit that receives the signals from the SIC and performs the necessary functions to prepare the X-ray source 102 for the required intensity level for the next pulse. In one embodiment, the X-ray source 102 further comprises an apparatus and method to physically change the intensity level of the source for the next pulse. In yet another embodiment, the X-ray source 102 further comprises a reference/monitor detector 114, which is read on each pulse to provide the exact intensity of the source during that pulse. Since monitor detectors are well-known to those of ordinary skill in the art for use with X-ray sources, they will not be described in detail herein.

In a pulsed linear-accelerator-based x-ray source, source intensity depends on three factors: the pulse duration, the peak current of electrons in the linac, and the pulse rate. In a first and preferred embodiment, the source intensity is modulated by changing the duration of the pulse, as described in greater detail below with respect to FIG. 3. Changing just the pulse duration as a method of modulating the X-ray intensity avoids a number of complications. Changing the pulse rate (number of pulses per second) is possible but requires major modifications to the inspection system operation. Changing the peak current of electrons in the accelerator is also possible, but this results in a change of an accelerator property called beam loading, as described below, and this affects the energy of the accelerated electrons. When changing just the pulse duration, the energy is relatively unaffected.

In a second embodiment, the source intensity is modulated by changing the peak current. Changing the peak current, however, also leads to a change in beam loading: while the electrons are drawing energy out of the accelerator structure, the available energy drops and subsequently, the electrons gain less energy. A change in the peak current changes the number of electrons being accelerated, which changes the beam loading, and thus, the amount of energy available for acceleration. A change in beam loading results, therefore, in a change in the final energy to which the electrons are accelerated. It is possible to use additional electronics to compensate for this by modifying modulator and RF source settings.

In a third embodiment, the source intensity is modulated by changing the number of pulses per second. While this method may be used with the present invention, conventional X-ray radiography systems use a single linac pulse to produce one column of pixels in the radiography image. Thus, there is a direct correspondence between the number of pulses per second and the image resolution in the longitudinal direction (i.e. along the scan direction) in conventional systems. In order to use this method, the present invention would have to be capable of producing many more pulses per second than conventional sources, and the detector system would have to integrate signals from different pulses over fixed time periods to produce one column of image data., i.e. each column of the image would now be the sum of a number of X-ray pulses, where before every pulse was used as a column in the image.

Using an intensity-modulated X-ray source is advantageous in that:

- If the OSP of the intensity-modulated source is equivalent to a conventional linear accelerator X-ray source, then the average amount of radiation produced by the intensity-modulated source will be reduced, on average, by a significant factor (as discussed above) since the required X-ray intensity will be smaller for the lower density areas of the cargo.
- The OSP of the intensity-modulated source may be chosen to be a factor F higher than that of an equivalent conventional linac X-ray source, such that the average amount of radiation produced by the intensity-modulated source will be approximately the same as for the conventional source. For a 6 MeV source, a factor F=4 accomplishes this goal. In fact, the radiation footprint is actually somewhat lower than for the conventional source because, on average, this increase by a factor of 4 is needed only for small sections of the image. The penetration capability for dense cargo will, however, have increased by the equivalent of about 5 cm of steel, which represents approximately a 13% improvement over the state-of-the-art penetration capability of about 40 cm of steel using a 6 MeV X-ray source, as measured using lead bricks behind steel plates.
- There are several possible configurations between these two extremes. For example, but not limited to such example, it is possible to decrease the average radiation footprint by a factor of about 1.65, while still gaining 2.5 cm of steel-equivalent in penetration capability for a 6 MeV X-ray source.

In operation, the cargo inspection system uses the source intensity modulation systems and methods of the present invention as follows. An OSP is chosen so that it corresponds to one of the possibilities outlined above, and more specifically, equivalent to a conventional source, a factor of four (for a 6 MeV source) higher than the equivalent source, or somewhere between these two options. For the intensity-modulated source, the OSP is defined as the maximum intensity it is allowed to put out (which may still be less than the rated intensity).

The intensity-modulated system is then initialized to its lowest intensity setting. A single vertical line scan is then performed by the system at this intensity. The Source Intensity Controller electronics, described above, in the cargo inspection system determines if any of the detectors of the system received less than a certain pre-determined threshold signal, A. If so, the electronics instructs the intensity-modulated source system to increase its output by some factor, for example, a factor of two. A second vertical line scan is performed at the new, higher, intensity. If any of the detectors still receive less than the threshold signal, A, the electronics repeats the request to the intensity-modulated source for an increase of a factor of two in intensity. This process repeats until either the intensity modulated source is at its OSP, or until the signal in each detector is above the threshold signal A.

Optionally, if the minimum transmission level is above predetermined and preprogrammed first level A but below predetermined and preprogrammed second level, B a different signal instructs the source to stay at the same intensity. It should be noted, however, that this signal may be eliminated and the source will stay at the same intensity by default and absent instruction from the signal.

If the minimum transmission level is above predetermined and preprogrammed second level B, a signal instructs the source to decrease its X-ray intensity for the next pulse.

Optionally, the X-ray scanning system can include two detector arrays, adjacent to each other. The first array is specifically configured to measure the required source intensity for the next pulse (and not the transmission image), and second array is specifically configured to measure the transmission image (and not the required source intensity). Using this technique, the required intensity for the next pulse can be measured precisely. While increasing the number of detector arrays can increase the cost, it can also improve throughput through the inspection system. One of ordinary skill in the art would appreciate that other specialized detector arrays can be added and incorporated into the present invention.

In an alternate embodiment, instead of requesting a fixed factor increase from the source, it is possible to send a direct signal to the source communicating the required intensity for the next pulse. Thus, while the present invention is described with respect to changing the source intensity by a given factor at a time, it is possible to specify a particular intensity change to the source.

The ideal intensity of the source should be such that the minimum detector level equals A at all times. Therefore, the appropriate intensity $I_{new}$ for the next pulse should be:

$$I_{new}=I_{cur}*A/D_{min} \quad (1)$$

where $I_{new}$ is bounded by the minimum and maximum possible intensities $I_{min}$ and $I_{max}$ of the source, $D_{min}$ is the minimum measured detector level, and $I_{cur}$ is the current source intensity level. This new intensity value can, in one embodiment, be sent directly to the IMAXS source across an electrical connection in either analog or digital form, or across an optical connection in digital form. The equation above, however, assumes that the x-ray source is capable of producing arbitrary intensities, or at least intensities close to those desired, in the range $I_{min}$ to $I_{max}$. Further, such finely tuned intensity adjustments do not significantly improve performance. In fact, at the threshold between a light area (low absorption in the cargo) in the image and a dark area (high absorption), such fine-tuned intensity adjustments can be detrimental: the intensity adjustments are, after all, based on the detector levels measured during the previous pulse. It is better to make larger steps in intensity (i.e. factors of two or so), to anticipate the case that more intensity may be needed than expected from the detector levels measured in the previous pulse.

Thus, in one embodiment, a more appropriate intensity is calculated using the following formula:

$$I_{new} = I_{max} * \exp(-\log(2) * \text{floor}[\log((I_{max} * D_{min})/(A * I_{cur}))/\log(2)]) \quad (2)$$

Here, the function floor(x) finds the nearest integer smaller than x. Note that formula (2) reduces to formula (1) if the function floor( ) is removed. Using formula (2) the intensity is thus converted to a power of 2 times the maximum intensity (although other factors could be chosen than factors of 2). This new intensity, after bounding it between $I_{min}$ and $I_{max}$, can then be sent directly by electrical or optical connection to the x-ray source. Note that $I_{max}$ may be arbitrarily normalized to 1, where 1, by convention, is then taken to be the OSP of the IMAXS source. Further note, that for both of the above formulas, the SIC must keep track of the current intensity, $I_{cur}$. And, finally, note, that no intensity change occurs unless $D_{min} > 2*A$, i.e., effectively the threshold B is set to be 2*A.

Another signal is used to instruct the source to perform the X-ray pulse itself. This last signal is sent after sufficient time has elapsed for the source to settle in its new intensity setting. This process repeats until the end of the scan, and the source returns to its minimum intensity setting.

The present invention will now be described, by way of example only, in use with a cargo inspection system that employs a conventional 6 MeV linac x-ray source. The intensity modulated x-ray source technology as described in the present invention may be used with any linac energy, typically ranging from 1 to 15 MeV.

Figure 1B:
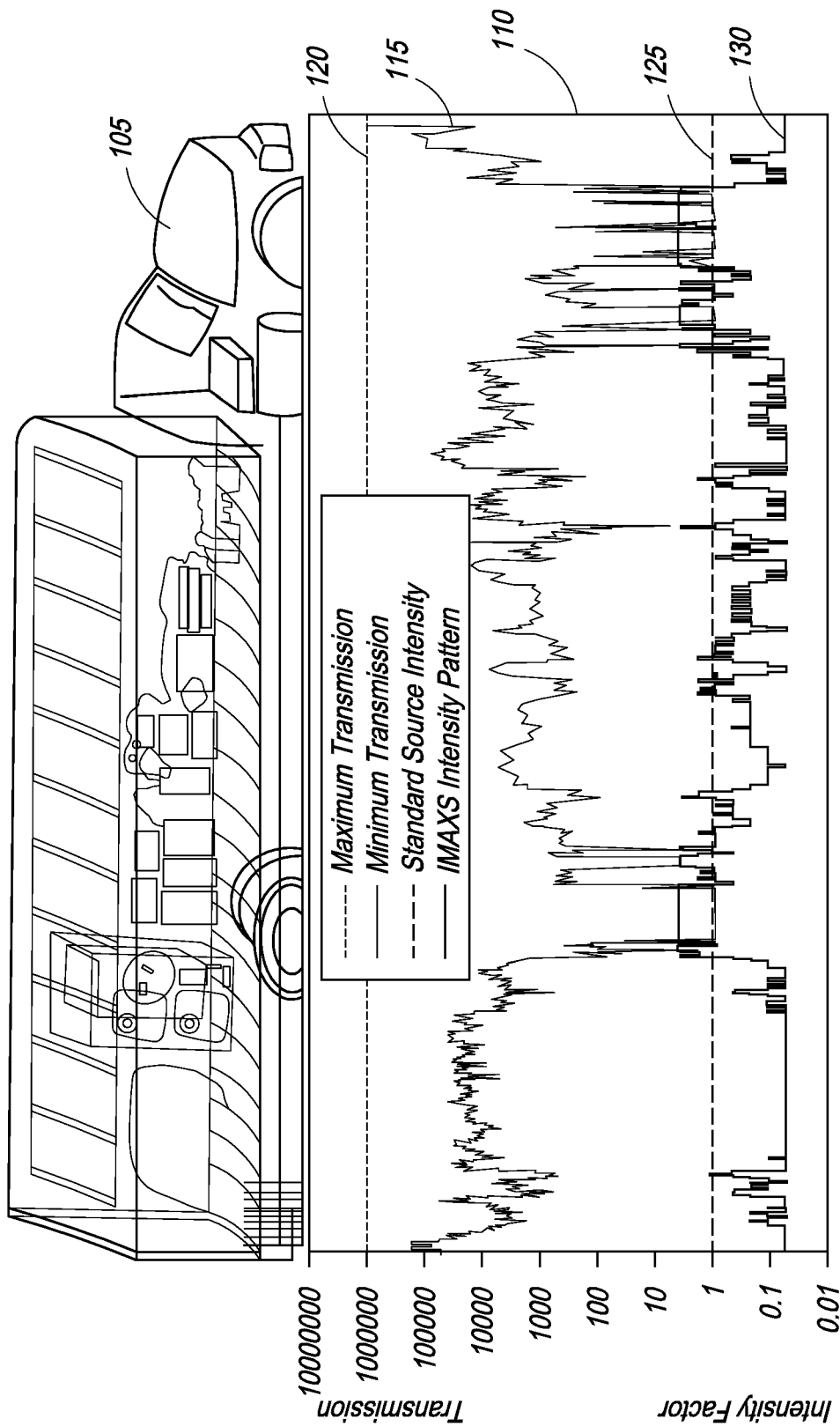
FIG. 1b shows a cargo X-ray image and line graph obtained using a cargo inspection system that employs a conventional 6 MeV linear accelerator (linac) x-ray source, at a fixed intensity and another line graph that would be obtained by using an intensity modulated source.

FIG. 1b shows a cargo X-ray image 105, obtained using a cargo inspection system that employs a conventional 6 MeV linac X-ray source. The corresponding graph 110 shows minimum transmission pattern 115, maximum transmission line 120, standard source intensity line 125, and intensity-modulated source pattern 130, where the transmission is measured in vertical columns in the X-ray image having one column per X-ray pulse, over the course of the image. The intensity-modulated source pattern 130 depicts a source intensity line structure if an intensity modulated X-ray source was used. As shown in the image, there are many areas where the minimum transmission is fairly high (1,000-10,000 arbitrary units in the image) and only a few areas where the minimum transmission is very low. Conventional sources use the same fixed intensity 125, whereas the intensity-modulated source may have the intensity profile 130.

Figure 2:
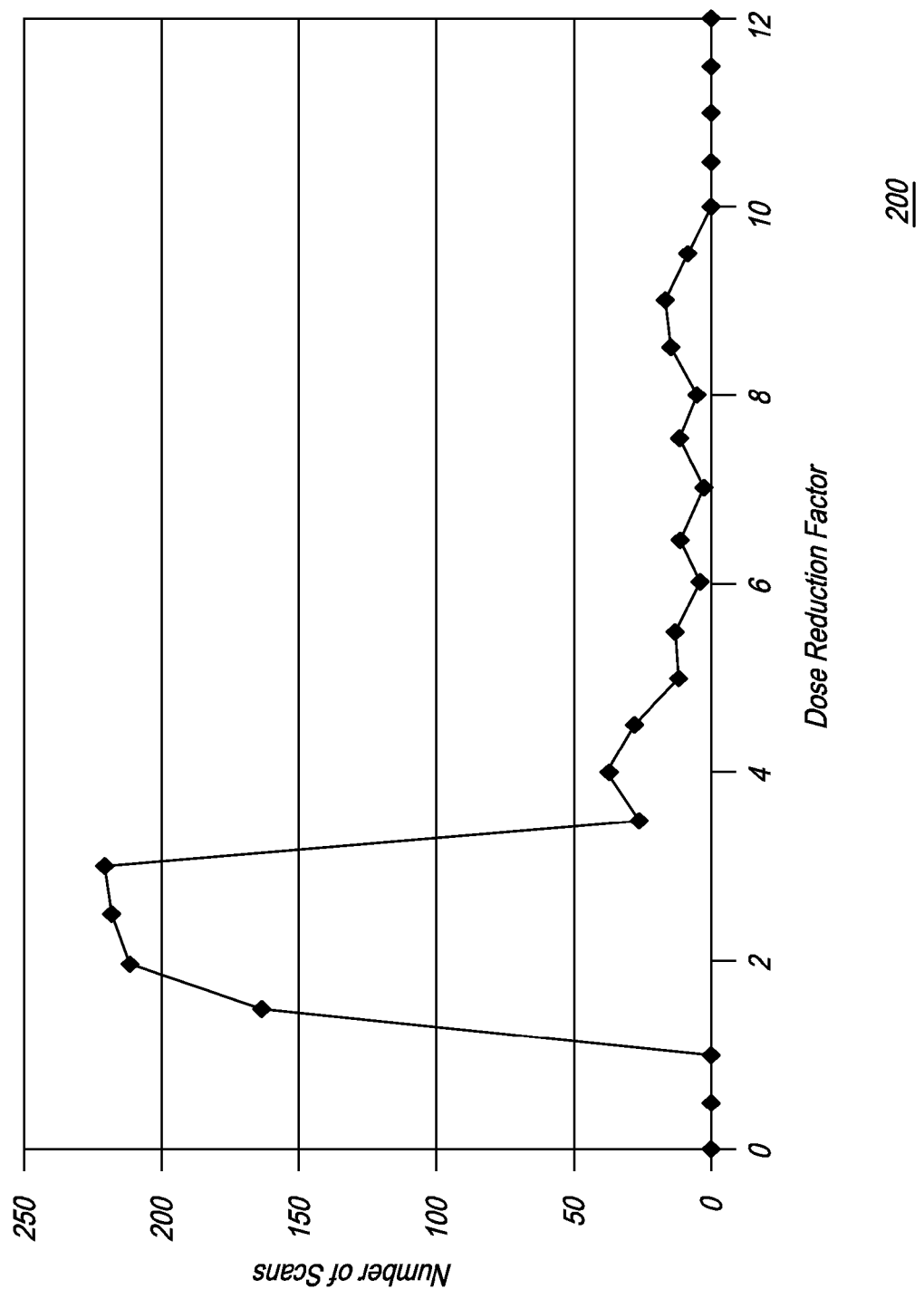
FIG. 2 is a graph of the results of an analysis of over 1000 images obtained with a conventional imaging system showing the radiation footprint reduction factor if the system had been employing the intensity-modulating system of the present invention.

FIG. 2 is a graph 200 of the results of a calculation of the effect an IMAXS source would have had, using 1000 images obtained with a Rapiscan Systems, Inc. MSCS Eagle® system, which has a fixed-intensity 6 MeV x-ray source. As described above and shown in the graph, the average dose would have been reduced by a factor of 3, while maintaining equivalent image penetration. Further analysis of these images shows, that, with the same radiation footprint as a conventional source, the imaging penetration of a system using the intensity-modulated source of the present invention would have been approximately two inches of steel or steel-equivalent better.

As mentioned above, the present invention is capable of modulating the intensity of the source on a pulse-to-pulse basis (i.e. in a few milliseconds). In one embodiment, the X-ray source is modified so that the system is capable of pulse-to-pulse variation of intensity. In one embodiment, the X-ray source further comprises an SICR, which is an electronics circuit which receives the signals from the SIC and performs the necessary functions to prepare the source for the required intensity level for the next pulse. Also as mentioned above, in one embodiment, the source intensity is modulated by changing the duration of the pulse.

By way of background, pulsed linear electron accelerators usually have one of two types of electron guns: a diode gun or a gridded gun, also known as a triode gun. In the case of a diode gun, a negative high voltage pulse on the cathode causes electrons to be emitted. In the case of a triode gun, the cathode is kept at a smaller, fixed negative high voltage, which by itself is insufficient to emit the electrons. A grid placed in front of the cathode is pulsed with a relatively small positive voltage. The combined voltages of the cathode and grid allow electrons to escape from the cathode. In both cases, if a simultaneous RF pulse is present in the accelerating structure, the electrons are accelerated and eventually strike the target, creating X-rays. These gun designs are independent of the type, gradient and length of the accelerator structure and therefore work for any linac energy and for X-band as well as S-band.

Figure 3:
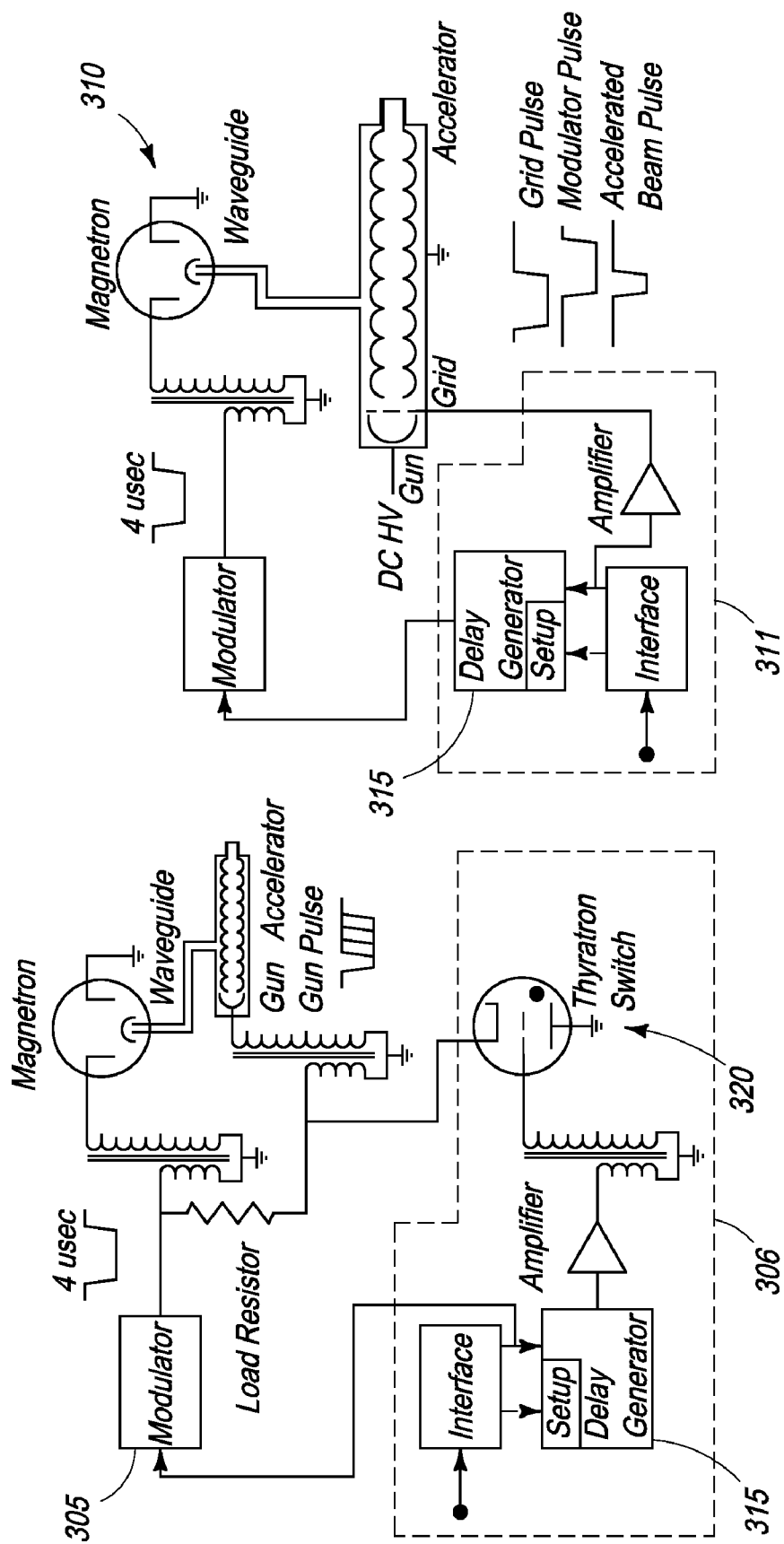
FIG. 3 shows diagrams of the circuitry involved in two types of electron guns.

FIG. 3 shows diagrams of the circuitry involved in both types of electron guns. Referring now to FIG. 3, diagram 305 shows the circuit for an accelerator with a diode gun and diagram 310 shows the circuit for an accelerator with a triode or gridded gun. FIG. 3 also depicts exemplary designs of additional retrofit circuitry 306 and 311 that allow for both types of electron guns to be used with the intensity-modulated source capability of the present invention. It should be noted that the designs are only exemplary and that the present invention is not limited to such designs.

As shown in FIG. 3, both retrofitting circuits 306 and 311 employ a delay generator 315. Between pulses, information from the inspection system detector array is used to preset delay generator 315 to a certain delay value, which, in one embodiment, ranges from 0 to the width of the RF pulse of the accelerator. If a diode gun circuit arrangement 305 is employed, the gun pulse is clamped to ground using a thyratron 320 after the delay, effectively shortening the pulse. Here, a shorter delay will cause fewer electrons to be generated and therefore decrease the intensity. If the triode gun circuit 310 is employed, a slightly different method is used—here, the delay is used to offset the RF pulse in time from the grid pulse. In this case, the same number of electrons is generated in each pulse, but only the electrons that are emitted within the RF pulse are accelerated. Varying the delay here causes a change in overlap between the grid and RF pulses and therefore a change in the number of accelerated electrons and in turn a change in intensity. Another triode gun choice is to change the injected pulse width by changing the pulse width of the grid pulse, thus reducing the injection of electrons into the accelerator. In a preferred embodiment, the triode or gridded gun 310 is employed as it has a relatively low grid voltage and can be timed more accurately.

While the intensity modulated source systems and methods have been described above with respect to a fixed, portal inspection system, it is also possible to use the intensity-modulated source of the present invention with mobile (i.e. truck-mounted) applications. In mobile applications, however, shielding weight is one of the limiting factors for the possible X-ray sources that can be used, because of limits on the maximum truck and per-axle weights. Higher energy sources require more shielding and a heavier beam stop behind the detector array. Therefore, currently available mobile inspection systems have a maximum source energy of ~4.5 MeV. Since the intensity-modulated source of the present invention can lower the overall radiation footprint of the imaging system, it is possible to use a higher energy source with the same beam stop. Thus, in using the present invention with mobile applications, it may be possible to use a 6 MeV or higher source in place of the conventional 4.5 MeV source.

Traditionally, the shielding for a linear accelerator consists mainly of lead, with the exception of a tungsten collimator close to the target. Lead is preferred as it is cheaper, however, the shielding weight of mostly-lead shielding is much greater than it would be for all-tungsten shielding, as will be explained below.

Figure 4A:
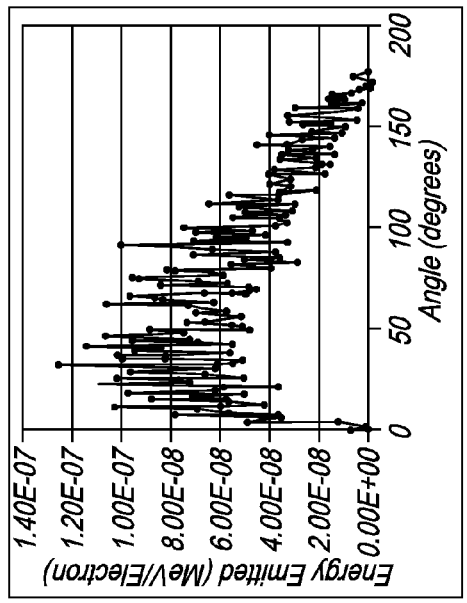
FIGS. 4a, 4b, and 4c shows the results of a simulation for a spherical lead shield of a certain thickness, an unshielded source, and a ratio of the two, respectively.
Figure 4B:
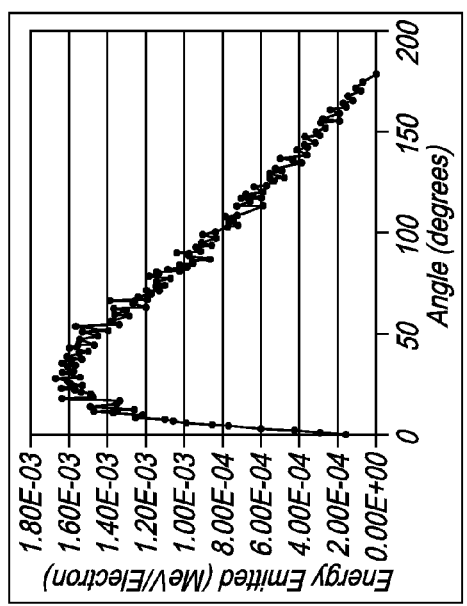
Figure 4C:
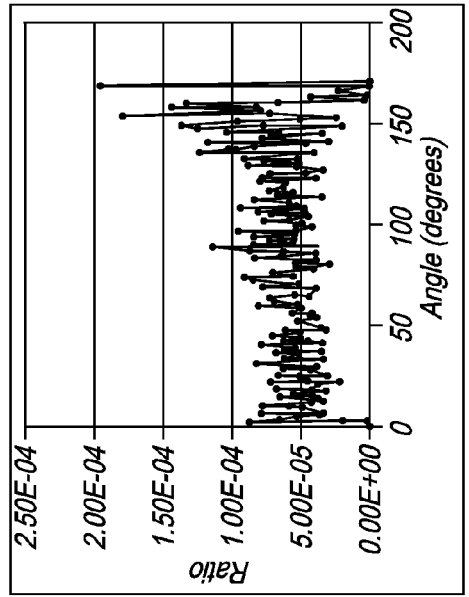

Ideally, shielding consists of a very dense, high-Z material in the form of a sphere around the target. Because the bremsstrahlung spectrum has higher intensity as well as higher energy in the forward direction, the sphere is not centered on the target, but offset by a distance D towards the front. The results of a simulation for a spherical lead shield of radius R=25 cm, target cavity radius r=2 cm and offset D=1.5 cm are presented in FIG. 4*a*, which shows the energy emitted from the source as a function of the angle with respect to the forward direction in graph 401. This should be compared to FIG. 4*b*, which shows the same for the unshielded source in graph 403. The ratio of the two graphs 401, 403 is given in FIG. 4*c*, which demonstrates (in graph 405) that, with these parameters, the radiation emitted is reduced in all directions by an essentially constant factor of $5.8 \cdot 10^{-5}$. If the required reduction factor is, say, $2.5 \cdot 10^{-6}$, we can find the radius $R_{desired}$ required for lead shielding by extrapolation using the formula:

$$R_{desired} = 25 \frac{\ln(2.5 \cdot 10^{-6})}{\ln(5.8 \cdot 10^{-5})} = 33 \text{ cm} \tag{3}$$

Figure 5B:
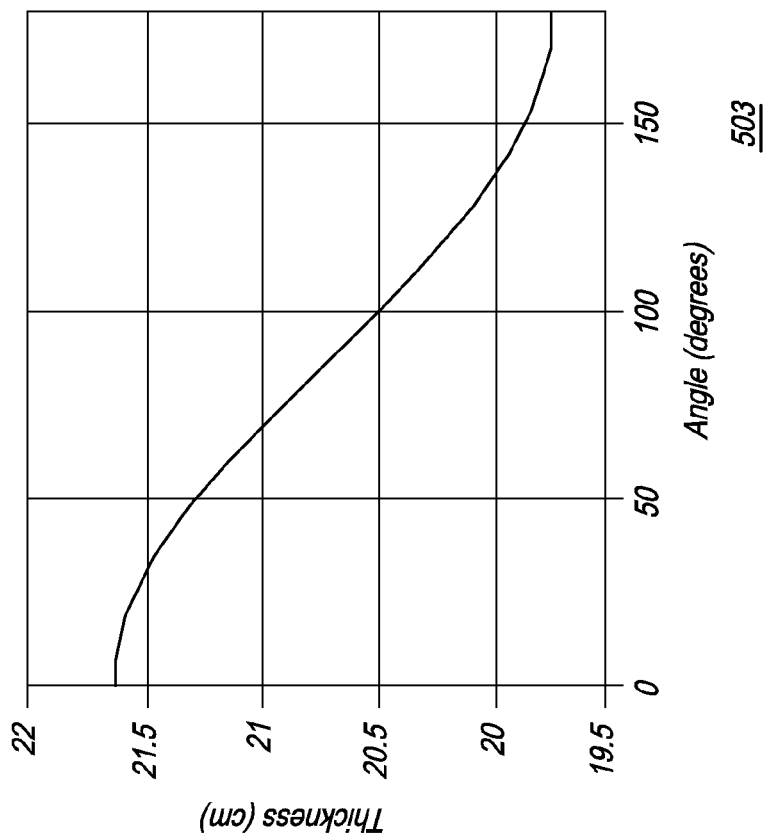
FIGS. 5a and 5b show the required amount of shielding resulting from the full shielding calculation for lead and tungsten, respectively.
Figure 5A:
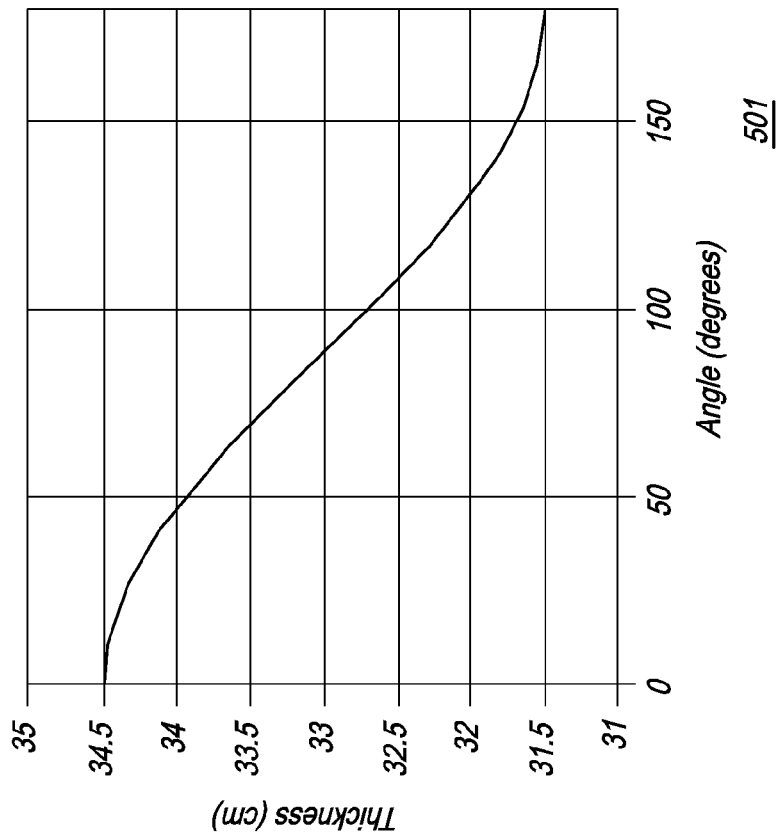

FIG. 5*a* shows the final results obtained using this type of simulation for lead. Shown in FIG. 5*a*, graph 501, is the amount of lead (in linear cm) needed to shield the target at each angle. Since in the energy region of interest the mass attenuation coefficients of lead and tungsten are very similar, the results for tungsten can be computed from those for lead by simple multiplication by the ratio of the specific weights. For 90%-pure tungsten, the specific weight is 17.1 g/cc, and the ratio is 0.664. The resulting computed amount of tungsten required (in linear cm) is shown in FIG. 5*b* in graph 503.

In re-examining the shielding requirements of 6 MeV sources for using the present invention with mobile applications, it can be concluded that a lead sphere of about 35 cm radius provides the same amount of shielding as a tungsten sphere of about 23 cm radius: the radius scales inversely with the specific weight. However, the volume of the sphere scales with the cube of the radius, and therefore with the inverse cube of the specific weight. Hence, the weight of the sphere scales with the inverse square of the specific weight. Thus the weight of the tungsten sphere (~900 kg) is considerably smaller than that of the lead sphere (~2000 kg).

Figure 6:
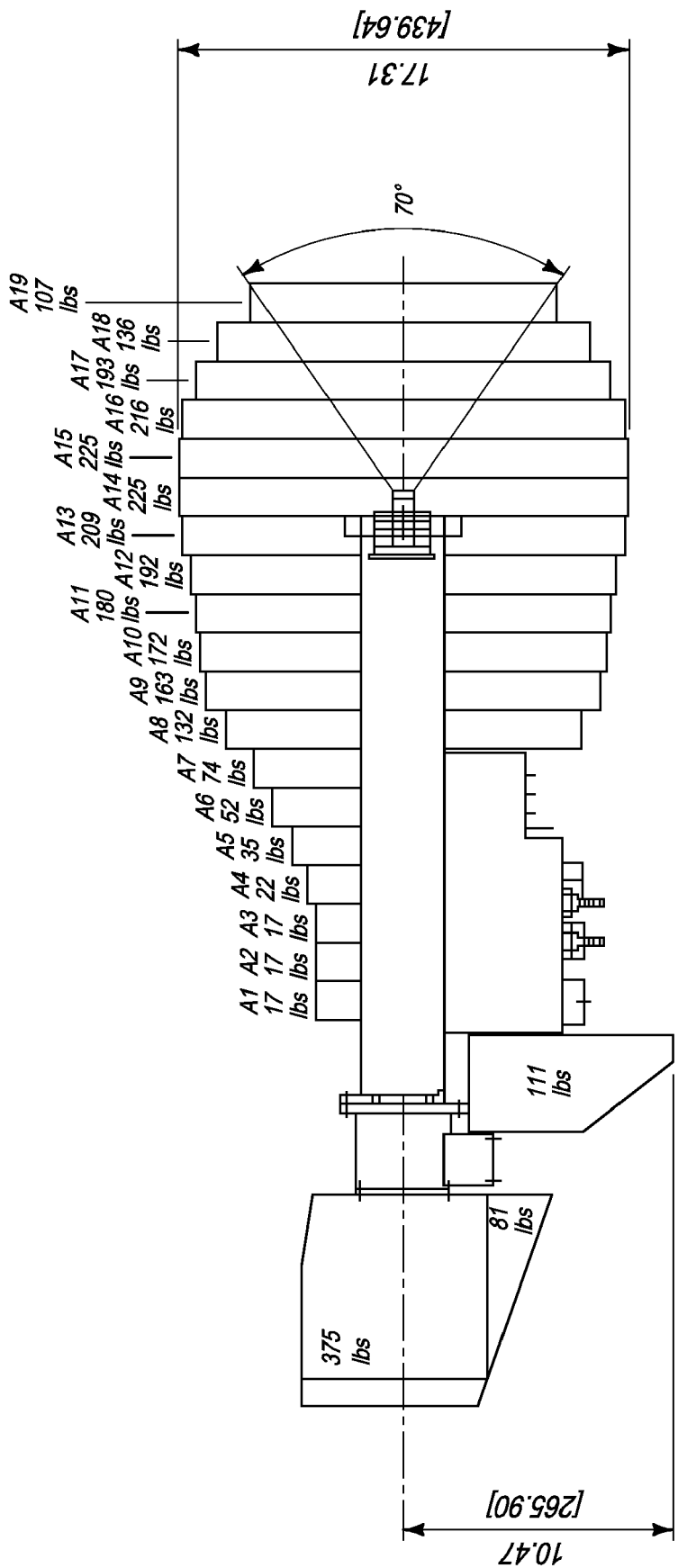
FIG. 6 depicts one embodiment of a shielding design for a 6 MeV X-band accelerator.

Further, completely spherical shields are impractical because of various obstacles, including the accelerator itself and connections for control signals, RF power and cooling liquids. FIG. 6 depicts one embodiment of a preferred shielding design 600 for a 6 MeV X-band accelerator. For this all-tungsten shield, the overall weight of the accelerator, including shielding, supports, enclosure and RF unit is estimated to be approximately 1540 kg. This should be compared to the weight of the currently used 4.5 MeV S-band accelerator (including supports, enclosure and RF unit) of approximately 2630 kg. Hence, all-tungsten shielding could reduce the weight of a 6 MeV X-band source by about 40% compared to a 4.5 MeV S-band source, leaving room to convert some of the (expensive) tungsten shielding back to lead.

Thus, in using an intensity-modulated source, it is possible to improve the radiation footprint of cargo inspection systems and improve imaging penetration performance considerably. It is also possible to employ shielding designs that will allow higher energy sources to be used in conjunction with the intensity-modulated source of the present invention in mobile inspection applications. Alternatively, even higher-energy accelerators could be used, while still having a lower or similar overall weight.

It should be noted that the intensity-modulating system and method of the present invention can be used with any inspection system. In particular, the system and method of the present invention can be used with an inspection system employing a dual-energy linear accelerator X-ray source, where the intensity is modulated concomitant with switching from a first energy to a second energy. In addition, the system and method of the present invention can be used with any inspection system employing a linear accelerator-based X-ray source, including portal systems, fixed systems, mobile systems, systems that operate in varying environments. Systems where personnel are exposed to scattered X-rays, such as portal systems, benefit most from the technology.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An X-ray scanning system comprising:
   a. A plurality of detectors;
   b. A controller, wherein said controller is configured to receive and identify a minimum X-ray transmission level detected by at least one, but fewer than all, of said plurality of detectors, wherein said controller compares said minimum X-ray transmission level to at least one predetermined threshold transmission level, and wherein, based on said comparison, said controller generates an adjustment signal; and
   c. An X-ray source, wherein said X-ray source receives said adjustment signal and is configured to adjust an X-ray pulse duration based on said adjustment signal.

2. The X-ray scanning system of claim 1 wherein said X-ray source is a linear accelerator having an energy in a range of 1 MeV to 15 MeV.

3. The X-ray scanning system of claim 1 wherein said X-ray source comprises a controller that receives said adjustment signal and, based on said signal, adjusts an X-ray pulse duration.

4. The X-ray scanning system of claim 1 wherein said controller compares said minimum X-ray transmission level to a first predetermined threshold and, if said minimum X-ray transmission level is below said first predetermined threshold, generates an adjustment signal that causes said X-ray source to increase an X-ray pulse duration.

5. The X-ray scanning system of claim 1 wherein said controller compares said minimum X-ray transmission level to a first predetermined threshold and second predetermined threshold and, if said minimum X-ray transmission level is above said first predetermined threshold but below said second predetermined threshold, generates an adjustment signal that causes said X-ray source to not modify an X-ray pulse duration.

6. The X-ray scanning system of claim 1 wherein said controller compares said minimum X-ray transmission level to a first predetermined threshold and second predetermined threshold and, if said minimum X-ray transmission level is above said second predetermined threshold, generates an adjustment signal that causes said X-ray source to decrease an X-ray pulse duration.

7. The X-ray scanning system of claim 1 wherein the controller comprises a computer having a processing unit and wherein said processing unit interfaces with an input/output board that receives signals from at least one of said plurality of detectors.

8. The X-ray scanning system of claim 1 wherein the processing unit is at least one of a field programmable gate array or an application specific integrated circuit.

9. The X-ray scanning system of claim 1 wherein the plurality of detectors comprise a first detector array, said first detector array being configured to measure a required source intensity for a subsequent X-ray pulse, and a second detector array, said second detector array being configured to measure a transmission image and not said required source intensity.

10. The X-ray scanning system of claim 1 wherein said X-ray source is configured to adjust a duration of a second X-ray pulse based on an adjustment signal generated from a first X-ray pulse occurring immediately prior to said second X-ray pulse.

11. A method of retrofitting an existing X-ray scanning system having an X-ray source and a plurality of detectors, wherein, during operation, said X-ray scanning system generates a radiation footprint and has a penetration capability defined by a distance into which radiation generated by said X-ray source penetrates an object, comprising installing a controller, wherein said controller is configured to receive and identify a minimum X-ray transmission level detected by at least one, but fewer than all, of said plurality of detectors, wherein said controller compares said minimum X-ray transmission level to at least one predetermined threshold transmission level, and wherein, based on said comparison, said controller generates an adjustment signal, said adjustment signal being configured to adjust an X-ray pulse duration based on said adjustment signal.

12. The method of claim 11 wherein said X-ray source is a linear accelerator having an energy in a range of 1 MeV to 15 MeV.

13. The method of claim 12 wherein, due to said retrofit, during operation, the penetration capability of said X-ray scanning system is increased by a distance ranging from 1 cm to 10 cm.

14. The method of claim 12 wherein, due to said retrofit, during operation, the radiation footprint of said X-ray scanning system is improved by a factor between 1 and 9.

15. The method of claim 11 wherein said controller compares said minimum X-ray transmission level to a first predetermined threshold and, if said minimum X-ray transmission level is below said first predetermined threshold, generates an adjustment signal that causes said X-ray source to increase an X-ray pulse duration.

16. The method of claim 11 wherein said controller compares said minimum X-ray transmission level to a first predetermined threshold and second predetermined threshold and, if said minimum X-ray transmission level is above said first predetermined threshold but below said second predetermined threshold, generates an adjustment signal that causes said X-ray source to not modify an X-ray pulse duration.

17. The method of claim 11 wherein said controller compares said minimum X-ray transmission level to a first predetermined threshold and second predetermined threshold and, if said minimum X-ray transmission level is above said second predetermined threshold, generates an adjustment signal that causes said X-ray source to decrease an X-ray pulse duration.

18. The method of claim 11 wherein the controller comprises a computer having a processing unit and wherein said processing unit interfaces with an input/output board that receives signals from at least one of said plurality of detectors.

19. The method of claim 11 wherein the plurality of detectors comprise a first detector array, said first detector array being configured to measure a required source intensity for a subsequent X-ray pulse, and a second detector array, said second detector array being configured to measure a transmission image and not said required source intensity.

20. The method of claim 11 wherein said X-ray source is configured to adjust a duration of a second X-ray pulse based on an adjustment signal generated from a first X-ray pulse occurring immediately prior to said second X-ray pulse.

* * * * *